(12) United States Patent
Shimada et al.

(10) Patent No.: US 11,446,290 B2
(45) Date of Patent: Sep. 20, 2022

(54) TREATMENT OF PAIN WITH SEROTONIN-3 RECEPTOR AGONIST

(71) Applicant: OSAKA UNIVERSITY, Suita (JP)

(72) Inventors: Shoichi Shimada, Suita (JP); Yukiko Yamamoto, Suita (JP); Makoto Kondo, Suita (JP)

(73) Assignee: OSAKA UNIVERSITY, Osaka (JP)

( * ) Notice: Subject to any disclaimer, the term of this patent is extended or adjusted under 35 U.S.C. 154(b) by 20 days.

(21) Appl. No.: 16/626,062

(22) PCT Filed: Jun. 27, 2018

(86) PCT No.: PCT/JP2018/024404
§ 371 (c)(1),
(2) Date: Dec. 23, 2019

(87) PCT Pub. No.: WO2019/004292
PCT Pub. Date: Jan. 3, 2019

(65) Prior Publication Data
US 2021/0145814 A1     May 20, 2021

(30) Foreign Application Priority Data
Jun. 28, 2017    (JP) ............................. JP2017-125874

(51) Int. Cl.
*A61K 31/4545*    (2006.01)
*A61P 25/04*    (2006.01)

(52) U.S. Cl.
CPC .......... *A61K 31/4545* (2013.01); *A61P 25/04* (2018.01)

(58) Field of Classification Search
CPC ....... A61K 31/4545; A61P 25/04; A61P 29/00
USPC ........................................................ 514/318
See application file for complete search history.

(56) References Cited

U.S. PATENT DOCUMENTS

| | | | |
|---|---|---|---|
| 4,409,228 | A | 10/1983 | Nisato et al. |
| 5,604,245 | A | 2/1997 | Krapcho et al. |
| 2004/0191312 | A1 | 9/2004 | Oksenberg et al. |

FOREIGN PATENT DOCUMENTS

| | | |
|---|---|---|
| JP | S5636481 | 4/1981 |
| JP | H7145166 | 6/1995 |
| WO | 2006021343 | 3/2006 |
| WO | 2016027757 | 2/2016 |

OTHER PUBLICATIONS

Bardin, L. et al.: Serotonin receptor subtypes involved in spinal antinociceptive effects of 5-HT in rats. Pain, vol. 86, pp. 11-18, 2000.*
Hains, B. et al.: Serotonin receptors 5-HT1A and 5-HT3 reduce hyperexcitability of dorsal horn neurons after chronic spinal cord hemisection injury in rat. Exp. Brain Res., vol. 149, pp. 174-186, 2003.*
Wilcox, G. et al.: Role of 5-HT3 receptors in pain modulation in the spinal cord. Central Peripheral 5-HT3 receptors, pp. 275-300, 1992.*
Bravo-Hernandez M, et al., "Role of peripheral and spinal 5-HT3 receptors in development and maintenance of formalin-induced long-term secondary allodynia and heperalgesia.", Pharmacology Biochemistry and Behavior, 2012, vol. 101, pp. 246-257.
Fu Y, et al., "Fluvoxamine increased glutamate release by activating both 5-HT3 and sigma-1 receptors in prelimbic cortex of chronic restraint stress C57BL/6 mice", Biochimica et Biophysics Acta (BBA)—MolecularCell Research, 2012, vol. 1823, pp. 826-837.
Guo W, et al., "Spinal 5-HT3 receptors mediate descending facilitation and contribute to behavioral hypersensitivity via reciprocal neuror-glial signaling cascade.", Molecular Pain, 2014, vol. 10, p. 35(1-18).
International Preliminary Report on Patentability (Chapter II of the Patent Cooperation Treaty) issued in the corresponding PCT application No. PCT/JP2018/024404 filed Jun. 27, 2018.
International Search Report issued in the corresponding PCT application No. PCT/JP2018/024404; dated Oct. 2, 2018.
Kondo M, Koyama Y, Nakamura Y, Shimada S., "A novel 5HT3 receptor-IGF1 mechanism distinct from SSRI-induced antidepressant effects", Molecular Psychiatry, advance online publication, Apr. 25, 2017, pp. 1-10.
Kondo M, Nakamura Y, Ishida Y, Shimada S., "The 5-HT3 receptor is essential for exercise-induced hippocampal neurogenesis and antidepressant effects", Molecular Psychiatry, 2015, 20: pp. 1428-1437.

(Continued)

*Primary Examiner* — Charanjit Aulakh
(74) *Attorney, Agent, or Firm* — Cantor Colburn LLP

(57) ABSTRACT

The present invention provides a drug for preventing or treating chronic pain and a method for preventing or treating chronic pain. A pharmaceutical composition comprising a serotonin-3 receptor agonist such as a compound represented by the following formula (I):

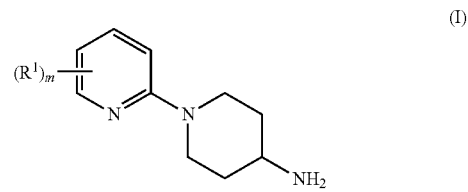

(I)

[wherein: m is an integer of 1 to 4; and $R^1$ is each independently selected from the group consisting of a hydrogen atom, a halogen atom, a methyl group optionally substituted with 1 to 3 halogen atom(s), a methoxy group optionally substituted with 1 to 3 halogen atom(s), and a methylthio group optionally substituted with 1 to 3 halogen atom(s)] or a pharmaceutically acceptable salt thereof is useful for preventing or treating chronic pain. The above pharmaceutical composition is also useful for preventing or treating acute pain. Further, the present invention provides a method for screening a compound for preventing or treating chronic pain, the method comprising measuring a serotonin-3 receptor agonist activity.

9 Claims, 3 Drawing Sheets

(56) References Cited

OTHER PUBLICATIONS

Kondo M, Nakamura Y, Ishida Y, Yamada T, Shimada S., "The 5-HT3A receptor is essential for fear extinction", Learning & Memory, 2014. 21(1): pp. 1-4.

Nakama-Kitamura M, Kitamura Y., "A novel conditioned nociceptive response In mice.", Brain Research, 2011, vol. 1406, pp. 8-17.

Nakama-Kitamura M, Kitamura Y., "The influence of fentanyl, fluvoxamine, and preferred olfactory stimuli on a novel conditioned nociceptive response in mice: a neuro-psycho-behavioral study.", Pain Research, 2012, vol. 27, pp. 153-164.

Sasaki M, et al., "Effects of 5-HT2 and 5-HT3 receptors on the modulation of nociceptive transmission in rat spina cord according to the formalin test.", European Journal of Pharmacology, 2001, vol. 424, pp. 45-52.

Uchida, Kunitoshi et al., "Antinociceptive action of fluvoxamine and antiallodynic action are achieved through another serotonin receptor", rograms and lecture abstracts of collaborative annual conference of the 27th Japanese Society of Biological Psychiatry and the 35th Japanese Society of Neuropsychopharmacology, 2005, p. 253(p. 2-66) (with its concise explanation).

Arnold et al., "Fibromyalgia and Chronic Pain Syndromes: A White Paper Detailing Current Challenges in the Field", Clinical Journal of Pain, vol. 32, No. 9, Sep. 1, 2016, pp. 737-746.

EPO Corrected Extended European Search Report for corresponding EP18823755.6 dated Apr. 17, 2020 which replaces Search Report of Apr. 2, 2020.

EPO Extended European Search Report for corresponding EP18823755.6 dated Apr. 2, 2020.

Indaco A et al., "Chronic and acute pain syndromes in patients with multiple sclerosis.—PubMed—NCBI", Abstract thereof, Jun. 16, 1994, XP055683631, Retrieved from the Internet: www.ncbi.nlm.nih.gov/pubmed/7992668, 2 pages.

Selvarajah et al., "The Contributors of emotional distress in painful diabetic neuropathy", Diabetes & Vascular Disease Research, May 12, 2014, vol. 11(4), pp. 218-225, London England.

Multidisciplinary Pain Management: Core Curriculum for Education in Pain, Chapter 4 "Pain and Brain" (edited by Japanese Association for the Study of Pain, Core Curriculum for Education in Pain editorialcommittee), Shinko Trading Company Ltd., Publication Department of Medical Books, p. 43-45 (with its concise explanation), Oct. 2016.

Liu et al., "Role of 5-HT receptors in neuropathic pain: potential therapeutic implications", Elsevier, Pharmacological Research 159 (2020) 104949; 16 pages.

\* cited by examiner

TREATMENT OF PAIN WITH SEROTONIN-3 RECEPTOR AGONIST

CROSS REFERENCE TO RELATED APPLICATIONS

This is the U.S. national stage of application No. PCT/JP2018/024404, filed on Jun. 27, 2018. Priority under 35 U.S.C. § 119(a) and 35 U.S.C. § 365(b) is claimed from Japanese Patent Application No. 2017-125874, filed Jun. 28, 2017; the disclosures of which are incorporated herein by reference.

TECHNICAL FIELD

The present invention relates to a drug for preventing or treating chronic pain and a method for preventing or treating chronic pain using a serotonin-3 receptor agonist. The present invention also relates to a drug for preventing or treating chronic pain and acute pain and a method for preventing or treating chronic pain and acute pain using a serotonin-3 receptor agonist. Further, the present invention relates to a method for screening a compound for preventing or treating chronic pain, the method comprising measuring a serotonin-3 receptor agonist activity.

BACKGROUND ART

In developed countries, many people are suffering from chronic pain, which is a social problem. Examples of chronic pain include pain having specific causative diseases or disorders such as chronic musculoskeletal pain and pain without apparent causative abnormality such as central dysfunctional pain (Non-patent Document 1). Among them, in case of central dysfunctional pain, pain sensitization is developed at central nervous system, and a patient continuously feels strong pain even after damage or inflammation in an affected area is cured. Meanwhile, International Association for the Study of Pain (IASP) defines pain as "An unpleasant sensory and emotional experience associated with actual or potential tissue damage, or described in terms of such damage". Namely, it is believed that when a brain feels pain, pain can be divided into sensory components which transmit pain sensation and emotional components which are affected by emotions such as anxiety, fear, and aversion. It is believed that central dysfunctional pain is mainly caused by emotional components of pain. However, the detailed mechanism of central dysfunctional pain has not been elucidated yet, and a sufficient therapeutic effect has not been achieved by existing therapeutic agents for pain such as opioids and non-steroidal anti-inflammatory drugs (NSAIDS). Also, opioids may cause problems such as dependence and non-steroidal anti-inflammatory drugs may cause problems such as side effects including gastrointestinal disorder.

Meanwhile, a compound represented by the following formula (SR57227A; compound name: 1-(6-chloropyridin-2-yl)piperidin-4-amine; hereinafter also referred to as "Compound A") etc. is known, and said compound etc. is also known to be a serotonin-3 receptor agonist (Patent Documents 1 and 2).

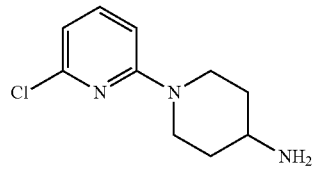 [SMILES: NC1CCN(c2cccc(Cl)n2)CC1]

However, it is not known that the serotonin-3 receptor agonists such as said compound are effective in preventing or treating chronic pain.

CITATION LIST

Patent Document

Patent Document 1: JPS56-36481A
Patent Document 2: JPH7-145166A

Non-Patent Document

Non-patent Document 1: Multidisciplinary Pain Management: Core Curriculum for Education in Pain, Chapter 4 "Pain and Brain" (edited by Japanese Association for the Study of Pain, Core Curriculum for Education in Pain editorial committee), Shinko Trading Company Ltd., Publication Department of Medical Books, p. 43-45

SUMMARY OF THE INVENTION

Problems to be Solved by Invention

The present invention has been made to solve the above problems in the prior art, and provides a drug for preventing or treating chronic pain and a method for preventing or treating chronic pain. The present invention also provides a drug for preventing or treating chronic pain and acute pain and a method for preventing or treating chronic pain and acute pain. Further, the present invention provides a method for screening a compound for preventing or treating chronic pain, the method comprising measuring a serotonin-3 receptor agonist activity.

Means to Solve Problems

The present inventors have earnestly studied to solve the above problems, as a result found that serotonin-3 receptor agonists have effects for preventing or treating chronic pain, and finally completed the present invention.

Namely, the present invention relates to the following [1] to [10].

[1]
A pharmaceutical composition comprising a serotonin-3 receptor agonist and a pharmaceutically acceptable carrier for preventing or treating chronic pain;

[2]
The pharmaceutical composition according to the above [1], wherein the chronic pain is central dysfunctional pain;

[3]
The pharmaceutical composition according to the above [1] or [2], wherein the chronic pain comprises pain derived from an emotional component;

[4]
The pharmaceutical composition according to any one of the above [1] to [3], wherein the serotonin-3 receptor agonist is a compound represented by the following formula (I):

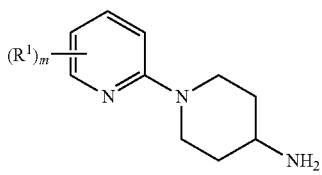

[wherein:
m is an integer of 1 to 4; and
$R^1$ is each independently selected from the group consisting of a hydrogen atom, a halogen atom, a methyl group optionally substituted with 1 to 3 halogen atom(s), a methoxy group optionally substituted with 1 to 3 halogen atom(s), and a methylthio group optionally substituted with 1 to 3 halogen atom(s)]
or a pharmaceutically acceptable salt thereof;
[5]
The pharmaceutical composition according to the above [4], wherein $R^1$ is each independently a halogen atom;
[6]
The pharmaceutical composition according to the above [4], wherein each $R^1$ is a chlorine atom;
[7]
The pharmaceutical composition according to any one of the above [4] to [6], wherein m is 1;
[8]
The pharmaceutical composition according to any one of the above [4] to [7], wherein the compound represented by formula (I) or a pharmaceutically acceptable salt thereof is a compound represented by the following formula (I'):

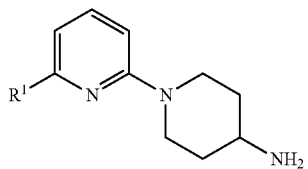

[wherein $R^1$ is the same as defined above]
or a pharmaceutically acceptable salt thereof;
[9]
The pharmaceutical composition according to any one of the above [1] to [3], wherein the serotonin-3 receptor agonist is a compound represented by the following formula:

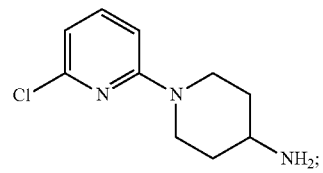 [SMILES: NC1CCN(c2cccc(Cl)n2)CC1]

[10] The pharmaceutical composition according to any one of the above [1] to [9] for preventing or treating chronic pain and acute pain; and
[11]
A method for screening a compound for preventing or treating chronic pain, the method comprising measuring a serotonin-3 receptor agonist activity.

The present invention also relates to the following [12] to [17].
[12]
A serotonin-3 receptor agonist for preventing or treating chronic pain;
[13]
A serotonin-3 receptor agonist for preventing or treating chronic pain and acute pain;
[14]
A method for preventing or treating chronic pain, the method comprising administering a serotonin-3 receptor agonist;
[15]
A method for preventing or treating chronic pain and acute pain, the method comprising administering a serotonin-3 receptor agonist;
[16]
Use of a serotonin-3 receptor agonist in the manufacture of a drug for preventing or treating chronic pain; and
[17]
Use of a serotonin-3 receptor agonist in the manufacture of a drug for preventing or treating chronic pain and acute pain.
Further, the present invention relates to the following [18] to [21].
[18]
A pharmaceutical composition comprising the compound represented by formula (I) or a pharmaceutically acceptable salt thereof and a pharmaceutically acceptable carrier for preventing or treating acute pain;
[19]
The compound represented by formula (I) or a pharmaceutically acceptable salt thereof for preventing or treating acute pain;
[20]
A method for preventing or treating acute pain, the method comprising administering the compound represented by formula (I) or a pharmaceutically acceptable salt thereof; and
[21]
Use of the compound represented by formula (I) or a pharmaceutically acceptable salt thereof in the manufacture of a drug for preventing or treating acute pain.

Effect of Invention

The serotonin-3 receptor agonist used as an active ingredient of the present invention targets different serotonin-3 receptors from the targets of existing therapeutic agents for pain, and thus has preventive or therapeutic effects on chronic pain on which a sufficient effect has not been achieved by conventional therapeutic agents for pain such as opioids and non-steroidal anti-inflammatory drugs. Also, the serotonin-3 receptor agonist used as an active ingredient of the present invention has preventive or therapeutic effects on central dysfunctional pain. Further, the serotonin-3 receptor agonist used as an active ingredient of the present invention has not only preventive or therapeutic effects on pain derived from a sensory component, but also preventive or therapeutic effects on pain derived from an emotional component. Thus, the present invention can provide a drug and a method for preventing or treating chronic pain on which a sufficient preventive or therapeutic effect has not been achieved by existing therapeutic agents for pain. Further, the serotonin-3 receptor agonist used as an active ingredient of the present invention also has preventive or therapeutic effects on acute pain. Also, according to the present invention, a compound for preventing or treating chronic pain can be screened by measuring a serotonin-3 receptor agonist activity.

MODE FOR CARRYING OUT THE INVENTION

Figure 1:
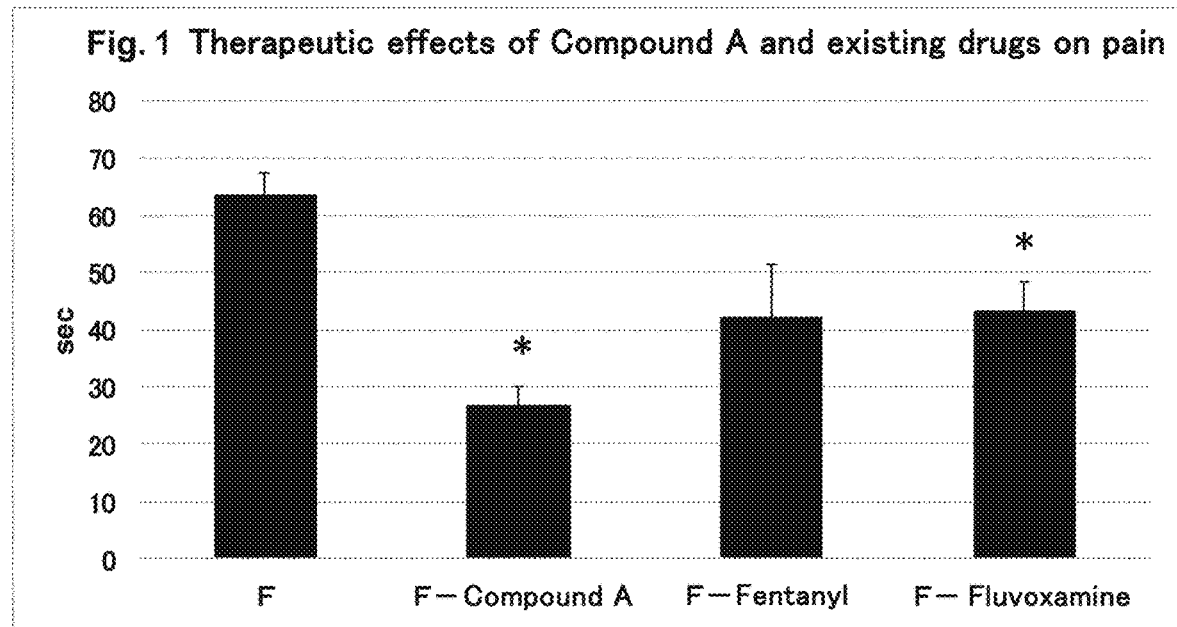
FIG. 1 This figure shows therapeutic effects of Compound A and existing drugs on pain. "F" shows a group to which only formalin was administered, "F-Compound A" shows a group to which Compound A (5 mg/kg) was administered before formalin administration, "F-Fentanyl" shows a group to which fentanyl (0.05 mg/kg) was administered before formalin administration, and "F-Fluvoxamine" shows a group to which fluvoxamine (10 mg/kg) was administered before formalin administration. In the figure, the symbol "*" means $p<0.05$ (vs. F (formalin administration group)).

Definition of each group in the present description may be appropriately combined with each other, unless otherwise specified.

Examples of the term "halogen atom" used in the present description include a fluorine atom, a chlorine atom, a bromine atom, and an iodine atom, and preferable examples thereof include a fluorine atom and a chlorine atom.

The term "chronic pain" used in the present description is long-lasting pain, and has a meaning usually used in this technical field. Examples thereof include, but are not limited to, neuropathic pain (for example, diabetic neuropathy and postherpetic neuralgia), nociceptive pain (for example, rheumatoid arthritis), and central dysfunctional pain (for example, fibromyalgia). In one embodiment, the serotonin-3 receptor agonist which is an active ingredient of the present invention is used in the prevention or treatment of central dysfunctional pain. In the present description, central dysfunctional pain refers to a pathological condition of pain without a causative structural abnormality.

The term "acute pain" used in the present description refers to pain which has a certain etiology and basically be ameliorated in the process of repair of causative wound etc., and has a meaning usually used in this technical field. Examples thereof include, but are not limited to, nociceptive pain (for example, traumatic pain or postoperative pain).

Also, it is believed that pain can be divided into sensory components caused by pain sensation of noxious stimuli, and emotional components caused by experiencing or learning noxious stimuli and potentiated by emotions such as anxiety, fear, and aversion (for example, Non-patent Document 1). The serotonin-3 receptor agonist which is an active ingredient of the present invention has not only preventive or therapeutic effects on pain derived from a sensory component, but also effects on pain derived from an emotional component, and is especially useful for preventing or treating said pain. In the present description, pain derived from an emotional component refers to pain not caused by a mechanical and chemical stimulus, but caused by anxiety and the like. In one embodiment, chronic pain includes pain derived from a sensory component. In another embodiment, chronic pain includes pain derived from an emotional component. In another embodiment, chronic pain includes pain derived from a sensory component and pain derived from an emotional component.

In the present description, "prevention" of pain and "preventing" pain refer to preventing pain in a subject at risk of developing pain.

In the present description, "treatment" of pain and "treating" pain refer to, for example, relieving, alleviating, ameliorating, or partially or completely eliminating pain in a subject suffering from pain.

The serotonin-3 receptor agonist which is an active ingredient of the present invention is a substance which binds to a serotonin-3 receptor to cause a similar effect to serotonin, and examples thereof include, but are not limited to, a compound represented by any one of the following formula (I), (II), (III), (IV), or (V), or a pharmaceutically acceptable salt thereof.

In one embodiment, the serotonin-3 receptor agonist which is an active ingredient of the present invention is a compound represented by the following formula (I):

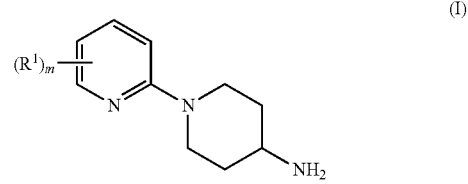

(I)

[wherein:
m is an integer of 1 to 4; and
$R^1$ is each independently selected from the group consisting of a hydrogen atom, a halogen atom, a methyl group optionally substituted with 1 to 3 halogen atom(s), a methoxy group optionally substituted with 1 to 3 halogen atom(s), and a methylthio group optionally substituted with 1 to 3 halogen atom(s)]
or a pharmaceutically acceptable salt thereof.

m is an integer of 1 to 4, preferably an integer of 1 to 3, more preferably an integer of 1 to 2, especially preferably 1.

Preferable examples of the halogen atom in $R^1$ include a fluorine atom and a chlorine atom, and especially preferable examples thereof include a chlorine atom.

Preferable examples of the methyl group optionally substituted with 1 to 3 halogen atom(s) in $R^1$ include a methyl group optionally substituted with 1 to 3 fluorine atom(s), and especially preferable examples thereof include a methyl group and a trifluoromethyl group.

Preferable examples of the methoxy group optionally substituted with 1 to 3 halogen atom(s) in $R^1$ include a methoxy group optionally substituted with 1 to 3 fluorine atom(s), and especially preferable examples thereof include a methoxy group and a trifluoromethoxy group.

Preferable examples of the methylthio group optionally substituted with 1 to 3 halogen atom(s) in $R^1$ include a methylthio group optionally substituted with 1 to 3 fluorine atom(s), and especially preferable examples thereof include a methylthio group and a trifluoromethylthio group.

In one embodiment, $R^1$ is each independently a halogen atom, and preferably each $R^1$ is a chlorine atom.

In another embodiment, m is 1. In another embodiment, $R^1$ is a halogen atom and m is 1.

In another embodiment, the compound represented by formula (I) or a pharmaceutically acceptable salt thereof is a compound represented by the following formula (I'):

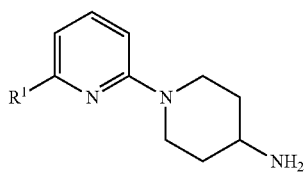

[wherein $R^1$ is the same as defined above]
or a pharmaceutically acceptable salt thereof.

In a preferable embodiment, the compound represented by formula (I) is a compound represented by the following formula:

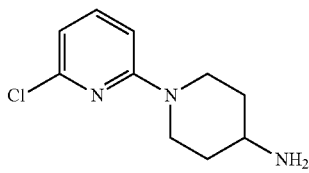 [SMILES: NC1CCN(c2cccc(Cl)n2)CC1]

(namely, Compound A (SR57227A, compound name: 1-(6-chloropyridin-2-yl)piperidin-4-amine)).

In another embodiment, the serotonin-3 receptor agonist which is an active ingredient of the present invention is a compound represented by the following formula (II):

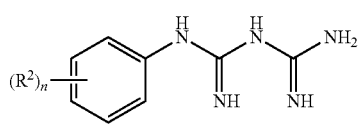

[wherein:
n is an integer of 1 to 4;
$R^2$ is each independently selected from the group consisting of a hydrogen atom, a halogen atom, a hydroxy group, a cyano group, a methyl group optionally substituted with 1 to 3 halogen atom(s), a methoxy group optionally substituted with 1 to 3 halogen atom(s), and a methylthio group optionally substituted with 1 to 3 halogen atom(s)] or a pharmaceutically acceptable salt thereof.

n is an integer of 1 to 4, preferably an integer of 1 to 3, more preferably an integer of 1 to 2, especially preferably 1.

Preferable examples of the halogen atom in $R^2$ include a fluorine atom and a chlorine atom, and especially preferable examples thereof include a chlorine atom.

Preferable examples of the methyl group optionally substituted with 1 to 3 halogen atom(s) in $R^2$ include a methyl group optionally substituted with 1 to 3 fluorine atom(s), and especially preferable examples thereof include a methyl group and a trifluoromethyl group.

Preferable examples of the methoxy group optionally substituted with 1 to 3 halogen atom(s) in $R^2$ include a methoxy group optionally substituted with 1 to 3 fluorine atom(s), and especially preferable examples thereof include a methoxy group and a trifluoromethoxy group.

Preferable examples of the methylthio group optionally substituted with 1 to 3 halogen atom(s) in $R^2$ include a methylthio group optionally substituted with 1 to 3 fluorine atom(s), and especially preferable examples thereof include a methylthio group and a trifluoromethylthio group.

In one embodiment, $R^2$ is each independently a hydrogen atom or a halogen atom, and preferably $R^2$ is each independently a hydrogen atom or a chlorine atom.

In another embodiment, n is 1. In another embodiment, $R^2$ is a hydrogen atom or a halogen atom and n is 1.

In another embodiment, the compound represented by formula (II) or a pharmaceutically acceptable salt thereof is a compound represented by the following formula (II'):

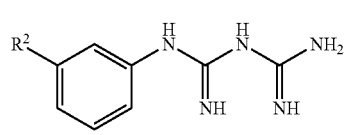

[wherein $R^2$ is the same as defined above]
or a pharmaceutically acceptable salt thereof.

In a preferable embodiment, the compound represented by formula (II) or a pharmaceutically acceptable salt thereof is a compound represented by the following formula:

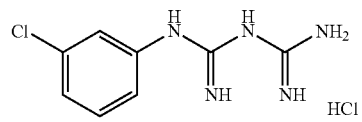 [SMILES: N=C(N)NC(=N)Nc1cccc(Cl)c1 ; Cl]

(compound name: m-chlorophenylbiguanide hydrochloride; hereinafter also referred to as "Compound B"); or a compound represented by the following formula:

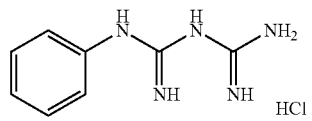 [SMILES: N=C(N)NC(=N)Nc1ccccc1 ; Cl]

(compound name: 1-phenylbiguanide hydrochloride; hereinafter also referred to as "Compound C").

In another embodiment, the serotonin-3 receptor agonist which is an active ingredient of the present invention is a compound represented by the following formula (III):

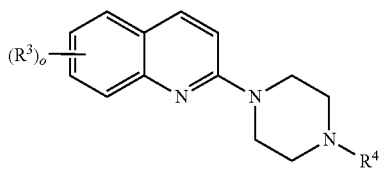

(III)

[wherein:
 o is an integer of 1 to 4;
 $R^3$ is each independently selected from the group consisting of a hydrogen atom, a halogen atom, a hydroxy group, a cyano group, a methyl group optionally substituted with 1 to 3 halogen atom(s), a methoxy group optionally substituted with 1 to 3 halogen atom(s), and a methylthio group optionally substituted with 1 to 3 halogen atom(s); and
 $R^4$ is selected from the group consisting of a hydrogen atom and a methyl group optionally substituted with 1 to 3 halogen atom(s)] or a pharmaceutically acceptable salt thereof.

o is an integer of 1 to 4, preferably an integer of 1 to 3, more preferably an integer of 1 to 2, especially preferably 1.

Preferable examples of the halogen atom in $R^3$ include a fluorine atom and a chlorine atom, and especially preferable examples thereof include a chlorine atom.

Preferable examples of the methyl group optionally substituted with 1 to 3 halogen atom(s) in $R^3$ include a methyl group optionally substituted with 1 to 3 fluorine atom(s), and especially preferable examples thereof include a methyl group and a trifluoromethyl group.

Preferable examples of the methoxy group optionally substituted with 1 to 3 halogen atom(s) in $R^3$ include a methoxy group optionally substituted with 1 to 3 fluorine atom(s), and especially preferable examples thereof include a methoxy group and a trifluoromethoxy group.

Preferable examples of the methylthio group optionally substituted with 1 to 3 halogen atom(s) in $R^3$ include a methylthio group optionally substituted with 1 to 3 fluorine atom(s), and especially preferable examples thereof include a methylthio group and a trifluoromethylthio group.

Preferable examples of the methyl group optionally substituted with 1 to 3 halogen atom(s) in $R^4$ include a methyl group optionally substituted with 1 to 3 fluorine atom(s), and especially preferable examples thereof include a methyl group.

In one embodiment, $R^3$ is each independently a hydrogen atom or a halogen atom, and preferably $R^3$ is each independently a hydrogen atom or a chlorine atom.

In another embodiment, $R^4$ is a hydrogen atom or a methyl group.

In another embodiment, o is 1. In another embodiment, $R^3$ is a hydrogen atom or a halogen atom, $R^4$ is a hydrogen atom or a methyl group, and o is 1.

In another embodiment, the compound represented by formula (III) or a pharmaceutically acceptable salt thereof is a compound represented by the following formula (III'):

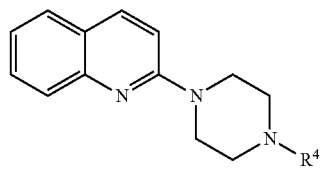

(III')

[wherein $R^4$ is the same as defined above]
or a pharmaceutically acceptable salt thereof.

In a preferable embodiment, the compound represented by formula (III) or a pharmaceutically acceptable salt thereof is a compound represented by the following formula:

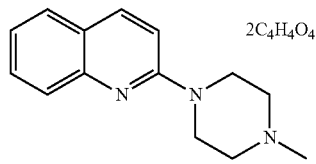 [SMILES: CN1CCN(c2ccc3ccccc3n2)CC1]

$2C_4H_4O_4$ (compound name: N-methylquipazine dimaleate; hereinafter also referred to as "Compound D"); or a compound represented by the following formula:

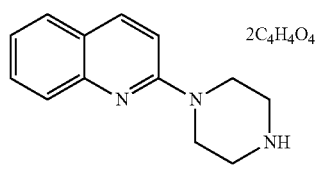 [SMILES: c1ccc2nc(N3CCNCC3)ccc2c1]

$2C_4H_4O_4$ (compound name: quipazine dimaleate; hereinafter also referred to as "Compound E").

In another embodiment, the serotonin-3 receptor agonist which is an active ingredient of the present invention is a compound represented by the following formula (IV):

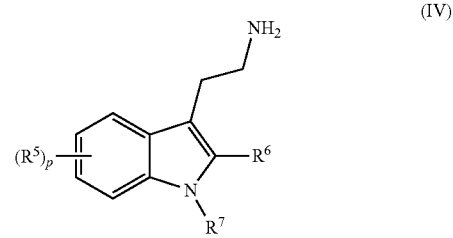

(IV)

[wherein:
 p is an integer of 1 to 4;
 $R^5$ and $R^6$ are each independently selected from the group consisting of a hydrogen atom, a halogen atom, a hydroxy group, a cyano group, a methyl group optionally substituted with 1 to 3 halogen atom(s), a methoxy group optionally substituted with 1 to 3 halogen atom(s), and a methylthio group optionally substituted with 1 to 3 halogen atom(s); and
 $R^7$ is selected from the group consisting of a hydrogen atom and a methyl group optionally substituted with 1 to 3 halogen atom(s)] or a pharmaceutically acceptable salt thereof.

p is an integer of 1 to 4, preferably an integer of 1 to 3, more preferably an integer of 1 to 2, especially preferably 1.

Preferable examples of the halogen atom in $R^5$ and $R^6$ include a fluorine atom and a chlorine atom, and especially preferable examples thereof include a chlorine atom.

Preferable examples of the methyl group optionally substituted with 1 to 3 halogen atom(s) in $R^5$ and $R^6$ include a methyl group optionally substituted with 1 to 3 fluorine atom(s), and especially preferable examples thereof include a methyl group and a trifluoromethyl group.

Preferable examples of the methoxy group optionally substituted with 1 to 3 halogen atom(s) in $R^5$ and $R^6$ include a methoxy group optionally substituted with 1 to 3 fluorine atom(s), and especially preferable examples thereof include a methoxy group and a trifluoromethoxy group.

Preferable examples of the methylthio group optionally substituted with 1 to 3 halogen atom(s) in $R^5$ and $R^6$ include a methylthio group optionally substituted with 1 to 3 fluorine atom(s), and especially preferable examples thereof include a methylthio group and a trifluoromethylthio group.

Preferable examples of the methyl group optionally substituted with 1 to 3 halogen atom(s) in $R^7$ include a methyl group optionally substituted with 1 to 3 fluorine atom(s), and especially preferable examples thereof include a methyl group.

In one embodiment, $R^5$ is each independently selected from the group consisting of a hydrogen atom, a halogen atom, a hydroxy group, and a cyano group, and preferably each $R^5$ is a hydroxy group.

In another embodiment, $R^6$ is selected from the group consisting of a hydrogen atom, a halogen atom, a hydroxy group, a cyano group, and a methyl group optionally substituted with 1 to 3 halogen atom(s), preferably a methyl group.

In another embodiment, $R^7$ is a hydrogen atom or a methyl group, preferably a hydrogen atom.

In another embodiment, p is 1. In another embodiment, $R^5$ is selected from the group consisting of a halogen atom, a hydroxy group, and a cyano group, $R^6$ is selected from the group consisting of a hydrogen atom, a halogen atom, and a methyl group optionally substituted with 1 to 3 halogen atom(s), $R^7$ is a hydrogen atom or a methyl group, and p is 1.

In another embodiment, the compound represented by formula (IV) or a pharmaceutically acceptable salt thereof is a compound represented by the following formula (IV'):

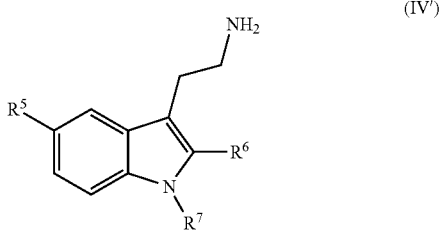

(IV')

[wherein $R^5$, $R^6$, and $R^7$ are the same as defined above] or a pharmaceutically acceptable salt thereof.

In a preferable embodiment, the compound represented by formula (IV) or a pharmaceutically acceptable salt thereof is a compound represented by the following formula:

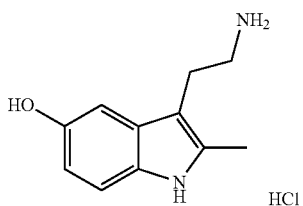

(compound name: 2-methyl-5-hydroxytryptamine hydrochloride; hereinafter also referred to as "Compound F").

In another embodiment, the serotonin-3 receptor agonist which is an active ingredient of the present invention is a compound represented by the following formula (V):

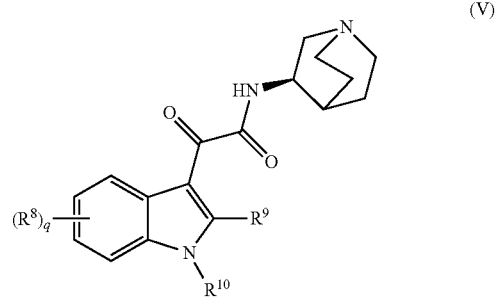

(V)

[wherein:
q is an integer of 1 to 4;
$R^8$ and $R^9$ are each independently selected from the group consisting of a hydrogen atom, a halogen atom, a hydroxy group, a cyano group, a methyl group optionally substituted with 1 to 3 halogen atom(s), a methoxy group optionally substituted with 1 to 3 halogen atom(s), and a methylthio group optionally substituted with 1 to 3 halogen atom(s); and
$R^{10}$ is selected from the group consisting of a hydrogen atom and a methyl group optionally substituted with 1 to 3 halogen atom(s)] or a pharmaceutically acceptable salt thereof.

q is an integer of 1 to 4, preferably an integer of 1 to 3, more preferably an integer of 1 to 2, especially preferably 1.

Preferable examples of the halogen atom in $R^8$ and $R^9$ include a fluorine atom and a chlorine atom, and especially preferable examples thereof include a chlorine atom.

Preferable examples of the methyl group optionally substituted with 1 to 3 halogen atom(s) in $R^8$ and $R^9$ include a methyl group optionally substituted with 1 to 3 fluorine atom(s), and especially preferable examples thereof include a methyl group and a trifluoromethyl group.

Preferable examples of the methoxy group optionally substituted with 1 to 3 halogen atom(s) in $R^8$ and $R^9$ include a methoxy group optionally substituted with 1 to 3 fluorine atom(s), and especially preferable examples thereof include a methoxy group and a trifluoromethoxy group.

Preferable examples of the methylthio group optionally substituted with 1 to 3 halogen atom(s) in $R^8$ and $R^9$ include a methylthio group optionally substituted with 1 to 3 fluorine atom(s), and especially preferable examples thereof include a methylthio group and a trifluoromethylthio group.

Preferable examples of the methyl group optionally substituted with 1 to 3 halogen atom(s) in $R^{10}$ include a methyl group optionally substituted with 1 to 3 fluorine atom(s), and especially preferable examples thereof include a methyl group.

In one embodiment, $R^8$ is each independently selected from the group consisting of a hydrogen atom, a halogen atom, a hydroxy group, and a cyano group, and preferably each $R^8$ is a hydrogen atom.

In another embodiment, $R^9$ is selected from the group consisting of a hydrogen atom, a halogen atom, a hydroxy group, a cyano group, and a methyl group optionally substituted with 1 to 3 halogen atom(s), preferably a hydrogen atom.

In another embodiment, $R^{10}$ is a hydrogen atom or a methyl group, preferably a methyl group.

In another embodiment, q is 1. In another embodiment, $R^8$ is a hydrogen atom or a hydroxy group, $R^9$ is a hydrogen atom or a methyl group, $R^{10}$ is a hydrogen atom or a methyl group, and q is 1.

In another embodiment, the compound represented by formula (V) or a pharmaceutically acceptable salt thereof is a compound represented by the following formula (V'):

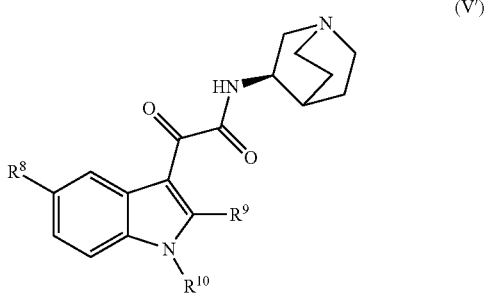

[wherein $R^8$, $R^9$, and $R^{10}$ are the same as defined above] or a pharmaceutically acceptable salt thereof.

In a preferable embodiment, the compound represented by formula (V) or a pharmaceutically acceptable salt thereof is a compound represented by the following formula:

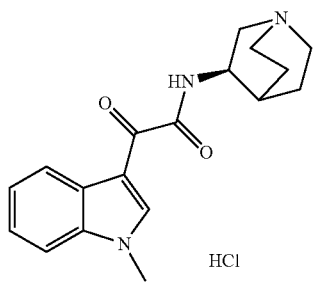 [SMILES: Cn1cc(C(=O)C(=O)N[C@H]2CN3CCC2CC3)c2ccccc21 ; Cl]

(RS56812 hydrochloride; compound name: (R)—N-(1-azabicyclo[2.2.2]oct-3-yl)-2-(1-methyl-1H-indol-3-yl)-2-(1-methyl-1H-indol-3-yl)-2-oxoacetamide hydrochloride; hereinafter also referred to as "compound G").

In one embodiment, the serotonin-3 receptor agonist which is an active ingredient of the present invention is the compound represented by any one of formula (I), (II), (III), (IV), or (V), or a pharmaceutically acceptable salt thereof. In another embodiment, the serotonin-3 receptor agonist which is an active ingredient of the present invention is the compound represented by any one of formula (I), (II), (IV), or (V), or a pharmaceutically acceptable salt thereof. In another embodiment, the serotonin-3 receptor agonist which is an active ingredient of the present invention is the compound represented by any one of formula (I'), (II'), (III'), (IV'), or (V'), or a pharmaceutically acceptable salt thereof. In another embodiment, the serotonin-3 receptor agonist which is an active ingredient of the present invention is the compound represented by any one of formula (I'), (II'), (IV'), or (V'), or a pharmaceutically acceptable salt thereof. In another embodiment, the serotonin-3 receptor agonist which is an active ingredient of the present invention is Compound A, B, C, D, E, F, or G. In another embodiment, the serotonin-3 receptor agonist which is an active ingredient of the present invention is Compound A, B, C, F, or G.

In a preferable embodiment, the serotonin-3 receptor agonist which is an active ingredient of the present invention is the compound represented by formula (I) or a pharmaceutically acceptable salt thereof. In a more preferable embodiment, the serotonin-3 receptor agonist which is an active ingredient of the present invention is the compound represented by formula (I') or a pharmaceutically acceptable salt thereof. In a still more preferable embodiment, the serotonin-3 receptor agonist which is an active ingredient of the present invention is Compound A.

When the serotonin-3 receptor agonist which is an active ingredient of the present invention such as the compound represented by any one of formula (I), (II), (III), (IV), or (V) has asymmetric carbon atom(s) in the molecule, it may exist as a plurality of stereoisomers (i.e., diastereoisomers or optical isomers) based on said asymmetric carbon atom(s). An active ingredient of the present invention encompasses both any one of these stereoisomers and mixtures thereof.

Also, the serotonin-3 receptor agonist which is an active ingredient of the present invention such as the compound represented by any one of formula (I), (II), (III), (IV), or (V) may also contain cis- and trans-isomers as geometrical isomers. Further, when the serotonin-3 receptor agonist which is an active ingredient of the present invention has axial chirality in the molecule, it may contain isomers based on the axial chirality. The present invention encompasses both any one of these isomers and mixtures thereof.

The serotonin-3 receptor agonist which is an active ingredient of the present invention such as the compound represented by any one of formula (I), (II), (III), (IV), or (V) encompasses compounds labeled with isotope(s) (for example, $^2H$, $^3H$, $^{13}C$, $^{14}C$, $^{15}N$, $^{18}F$, $^{32}F$, $^{35}S$, or $^{125}I$) or the like, and deuteratedproducts.

The serotonin-3 receptor agonist which is an active ingredient of the present invention such as the compound represented by any one of formula (I), (II), (III), (IV), or (V) may exist in the free form or in the form of a pharmaceutically acceptable salt thereof. Examples of the pharmaceutically acceptable salt include acid addition salts such as hydrochloride, hydrobromide, hydroiodide, sulfate, nitrate, phosphate, formate, acetate, propionate, fumarate, oxalate, malonate, succinate, methanesulfonate, ethanesulfonate, benzenesulfonate, toluenesulfonate, maleate, dimaleate, lactate, malate, tartrate, citrate, and trifluoroacetate; metal salts such as a lithium salt, a potassium salt, a calcium salt, a magnesium salt, a sodium salt, a zinc salt, and an aluminum salt; and base addition salts such as an ammonium salt, a diethanolamine salt, an ethylenediamine salt, a triethanolamine salt, and a triethylamine salt.

The serotonin-3 receptor agonist which is an active ingredient of the present invention such as the compound represented by any one of formula (I), (II), (III), (IV), or (V), or a pharmaceutically acceptable salt thereof includes all of inner salts or addition products thereof, solvates or hydrates thereof, cocrystals thereof, and the like.

One or more of the serotonin-3 receptor agonist(s) which is/are active ingredient(s) of the present invention such as the compound represented by any one of formula (I), (II), (III), (IV), or (V), or a pharmaceutically acceptable salt thereof may be directly administered to a patient; if necessary, however, an active ingredient of the present invention may be mixed with pharmaceutically acceptable carrier(s), and be provided as a formulation in a form well known to those skilled in the art.

Examples of said carriers include usually used carriers for pharmaceutical formulation such as excipients (for example, sugar derivatives such as mannitol and sorbitol; starch derivatives such as cornstarch and potato starch; and cellulose derivatives such as crystalline cellulose), lubricants (for example, metal stearates such as magnesium stearate; and talc), binders (for example, hydroxypropylcellulose, hydroxypropylmethylcellulose, and polyvinylpyrrolidone), disintegrants (for example, cellulose derivatives such as carboxymethylcellulose and carboxymethylcellulose calcium), preservatives (for example, para-hydroxybenzoates such as methylparaben and propylparaben; and alcohols such as chlorobutanol and benzyl alcohol), pH adjusters (for example, inorganic acids such as hydrochloric acid, sulfuric acid, and phosphoric acid; organic acids such as acetic acid, succinic acid, fumaric acid, and malic acid; and salts thereof), and diluents (for example, water for injection). Any one or a mixture of two or more of them may be used.

The serotonin-3 receptor agonist which is an active ingredient of the present invention such as the compound represented by any one of formula (I), (II), (III), (IV), or (V), or a pharmaceutically acceptable salt thereof may be mixed with the above carrier(s) if necessary, and then orally administered in a dosage form such as tablet, granule, capsule, powder, solution, suspension, and emulsion, or parenterally administered in a dosage form such as suppository, injection, intravenous drip, and inhalant.

The serotonin-3 receptor agonist which is an active ingredient of the present invention such as the compound represented by any one of formula (I), (II), (III), (IV), or (V), or a pharmaceutically acceptable salt thereof is formulated into the above dosage form, and then administered to a patient such as a human or an animal, preferably a human.

The dose and frequency of administration of the serotonin-3 receptor agonist which is an active ingredient of the present invention such as the compound represented by any one of formula (I), (II), (III), (IV), or (V), or a pharmaceutically acceptable salt thereof may be appropriately varied depending on conditions such as severity of pain, age, weight, and sex of a patient, type of drug, dosage form, and administration route. When administered to a human, the active ingredient is administered, for example, parenterally such as subcutaneously, intravenously, intraperitoneally, intramuscularly, and intrarectally at about 0.1 to 100 mg/kg weight, preferably about 1 to 50 mg/kg weight, especially preferably about 3 to 30 mg/kg weight, or orally at about 1 to 1000 mg/kg weight, preferably about 10 to 500 mg/kg weight, especially preferably about 30 to 300 mg/kg weight, per dose. Also, the frequency of administration may be once or more times per day such as once to three times, once to twice, and once per day.

Preferably, any one of the serotonin-3 receptor agonist which is an active ingredient of the present invention such as the compound represented by any one of formula (I), (II), (III), (IV), or (V), or a pharmaceutically acceptable salt thereof such as Compound A, B, C, D, E, F, and G may be administered alone, but if necessary, a combination of two or more of the serotonin-3 receptor agonist which is an active ingredient of the present invention may be administered, and further, the serotonin-3 receptor agonist which is an active ingredient of the present invention may be administered in combination with other drug(s) such as other therapeutic agents for pain. Examples of such other therapeutic agents for pain include opioids such as codeine, morphine, oxycodone, fentanyl, remifentanil, meperidine, buprenorphine, pentazocine, pethidine, butorphanol, tramadol, and naloxone; non-steroidal anti-inflammatory drugs such as aspirin, ethenzamide, diflunisal, Loxonin, ibuprofen, diclofenac, ketoprofen, naproxen, piroxicam, and indomethacin; and pregabalin and fluvoxamine, and pharmaceutically acceptable salts thereof.

When two or more of the serotonin-3 receptor agonist which is an active ingredient of the present invention are used in combination or the serotonin-3 receptor agonist which is an active ingredient of the present invention is used in combination with other drug(s), each drug may be administered simultaneously, sequentially, or separately. Also, each drug may be formulated as a compound drug comprising two or more drugs or a separate composition.

The serotonin-3 receptor agonist which is an active ingredient of the present invention may be a commercially available product or prepared according to a known method. For example, the compound represented by formula (I) or a pharmaceutically acceptable salt thereof may be prepared according to the method described in Patent Document 1 or 2. Also, Compound A, B, C, D, E, F, or G may be a commercially available product.

Further, the present invention relates to a method for screening a compound for preventing or treating chronic pain, the method comprising measuring a serotonin-3 receptor agonist activity.

The method for screening of the present invention comprises, for example, measuring a serotonin-3 receptor agonist activity regarding a compound library.

The compound library may be a known or unknown library. Examples of the known compound library include a compound library consisting of compounds already approved as foods (for example by Food and Drug Administration (FDA)) or drugs (for example by European Medicines Evaluation Agency (EMEA)) (for example, PRESTWICK CHEMICAL library which consists of compounds of which patent term has been expired), and a compound library consisting of compounds which have not yet been approved as foods or drugs.

Also, examples of the method for measuring a serotonin-3 receptor agonist activity include a method comprising expressing a subunit A of a serotonin-3 receptor, or cDNA of subunits A and B of a serotonin-3 receptor in cells (for example, oocytes of *Xenopus laevis* and HEK293 cells), and then electrophysiologically measuring the current flowed into the cells (Nakamura Y et al., Biochem Biophys Res Commun. 415(2) (2011) 416-20), or measuring fluorescence intensity by using fluorescent membrane-potential sensitive dye to measure the current flowed into the cells (Lummis S et al., Neuropharmacology 73 (2013) 241-246). In any method, a response obtained by administering a compound to the cells is investigated to measure a serotonin-3 receptor agonist activity.

The method for screening of the present invention may further comprise screening compounds on the basis of the measured serotonin-3 receptor agonist activity.

A compound obtained by the method for screening of the present invention has a serotonin-3 receptor agonist activity, and thus may be used in preventing or treating chronic pain.

The following Examples serve to more specifically illustrate the present invention, which should not intend to limit the present invention.

EXAMPLES

The following Experiments 1 to 5 have been carried out according to the method described in literatures (M Nakamura-Kitamura et al. Brain Research 1406 (2011), 8-17; and M Nakamura-Kitamura et al. Pain Research 27 (2012), 153-164) with minor modifications.

Male ddY mice of 5 weeks old (Japan SLC) were used in the experiments. Regarding the environment context as external senses and sensory stimuli such as tactile sense, visual sense, and feeling, a black cylindrical polypropylene box (diameter: 9.5 cm, height: 7 cm, with a round petri dish having a diameter of 8.5 cm at the bottom) and a translucent polypropylene box (14 cm (length)×9.5 cm (width)×5 cm (height), with a reticular plate at the floor) were used.

The mice were transferred to an experimental laboratory at day 0, placed into the black cylindrical box one by one, and acclimatized for 30 minutes.

Experiment 1: Therapeutic Effects of Compound a and Existing Drugs on Pain (Experimental Method)

At day 1, Compound A (5 mg/kg) or fluvoxamine (10 mg/kg) as a therapeutic agent for pain was intraperitoneally injected into a mouse 30 minutes before the administration of a pain inducer formalin (0.67%, 20 µL), or fentanyl (0.05 mg/kg) was intraperitoneally injected into a mouse 15 minutes before the formalin administration. In Experiments 1 to 5, each drug was dissolved into saline comprising 5% DMSO before use. Subsequently, each mouse was placed into the black round box, formalin was administered to the sole of the left foot, and the foot licking of the injected foot and biting were measured for 5 minutes. A mouse exhibits foot licking and biting when it feels pain. Thus, the therapeutic effect of each drug on pain can be evaluated by measuring the time of them. In the experiment, the group to which only formalin was administered (F) consisted of 17 mice, the group to which Compound A (5 mg/kg) was administered before formalin administration (F-Compound A) consisted of 7 mice, the group to which fentanyl (0.05 mg/kg) was administered before formalin administration (F-Fentanyl) consisted of 7 mice, and the group to which fluvoxamine (10 mg/kg) was administered before formalin administration (F-Fluvoxamine) consisted of 11 mice.

(Results)

Compound A could significantly suppress foot licking and biting caused by formalin. Especially, Compound A showed a more excellent therapeutic effect on pain as compared to the existing drugs such as fluvoxamine at a lower dose than the doses of these existing drugs (FIG. 1).

Experiment 2: Pain Derived from an Emotional Component (Experimental Method)

At day 1, each mouse was placed into the black round box (pain condition group) or the translucent box (control group). After 5 minutes, the mouse in each group received a sound stimulus (3000 Hz, 75 dB, 5 sec, 1 sec/1 sec, on/off, System 3 sound system, Bioresearch center), and formalin (0.67%, 20 µL) was immediately injected to the sole of the left foot of the mouse of each group (27 gauge needle). At day 2, each mouse was placed into the same box as that used at day 1, received a sound stimulus, and then formalin was injected into the sole of the right foot which was the opposite foot to that used at day 1.

At day 4 of the test phase, each mouse of the pain condition group and the control group was placed into the black round box. After 5 minutes, only the mouse of the pain condition group received a sound stimulus. Subsequently, saline instead of formalin was immediately injected into the sole of the left foot of each mouse, and foot licking of the sole of the right foot, which was the uninjected foot, and biting were measured for 5 minutes. The pain condition group (i.e., the group into which saline was injected at day 4 in the test phase under the same conditions as those at day 1 and 2) felt pain derived from conditioning, namely pain caused by experiencing and learning pain at day 1 and 2. Meanwhile, the control group (i.e., the group into which saline was injected in a new environment at day 4 in the test phase different from the environment at day 1 and 2) was exposed to the new environment, and thus did not feel pain derived from conditioning at day 1 and 2. In the experiment, the pain condition group consisted of 36 mice, and the control group consisted of 15 mice.

(Results)

Figure 2:
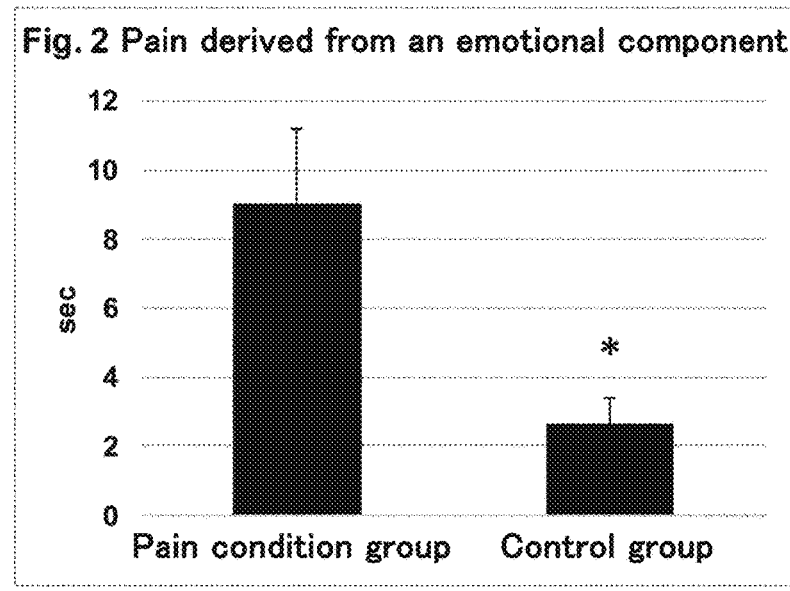
FIG. 2 This figure shows pain derived from an emotional component. The pain condition group represents a group which was exposed to the same conditions at day 4 in the test phase as the conditions at day 1 and 2, and the control group represents a group which was exposed to a new environment at day 4 in the test phase different from the environment at day 1 and 2. In the figure, the symbol "*" means $p<0.05$ (vs. pain condition group).

The mice of the pain condition group showed significantly increased seconds of foot licking and biting as compared to the mice of the control group (FIG. 2). Said difference was used as an indicator of pain derived from an emotional component in evaluating the therapeutic effects of pain derived from an emotional component in the following Experiment 3.

Experiment 3: Therapeutic Effects of Compound a and Existing Drugs on Pain Derived from an Emotional Component (Experimental Method)

At day 1, each mouse was placed into the black round box (pain condition group). After 5 minutes, each mouse received a sound stimulus (3000 Hz, 75 dB, 5 sec, 1 sec/1 sec, on/off, System 3 sound system, Bioresearch center), and formalin (0.67%, 20 µL) was immediately injected to the sole of the left foot of the mouse (27 gauge needle). At day 2, each mouse was placed into the same box as that used at day 1, received a sound stimulus, and then formalin was injected into the sole of the right foot which was the opposite foot to that used at day 1.

At day 4 of the test phase, vehicle (i.e., saline comprising 5% DMSO), Compound A (5 mg/kg or 10 mg/kg), or fluvoxamine (10 mg/kg) was intraperitoneally injected into each mouse 30 minutes before the administration of saline, or fentanyl (0.05 mg/kg) was intraperitoneally injected into each mouse 15 minutes before the administration of saline. Subsequently, each mouse was placed into the black round box. After 5 minutes, each mouse of the pain condition group received a sound stimulus. Subsequently, saline instead of formalin was immediately injected into the sole of the left foot of each mouse, and foot licking of the sole of the right foot, which was the uninjected foot, and biting were measured for 5 minutes. The difference between the result of each drug and the result of the vehicle administration group was calculated to evaluate the therapeutic effect of said drug on pain derived from an emotional component. In the experiment, the vehicle administration group consisted of 36 mice, the Compound A (5 mg/kg) administration group consisted of 7 mice, the Compound A (10 mg/kg) administration group consisted of 3 mice, the fentanyl (0.05 mg/kg) administration group consisted of 3 mice, and the fluvoxamine (10 mg/kg) administration group consisted of 7 mice.

(Results)

Figure 3:
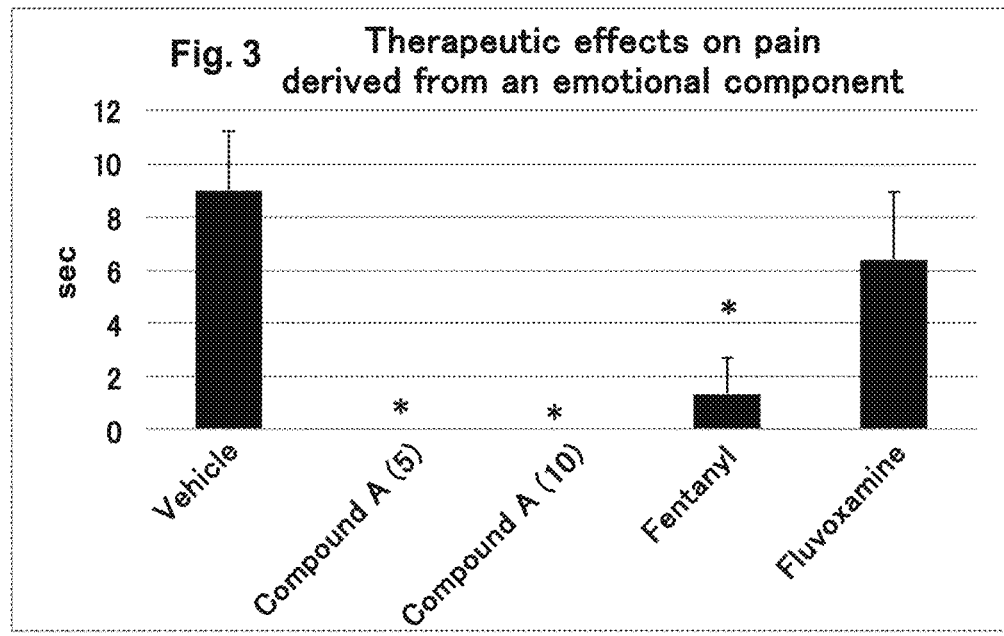
FIG. 3 This figure shows therapeutic effects of Compound A and existing drugs on pain derived from an emotional component. Each bar shows a vehicle administration group, a Compound A (5 mg/kg) administration group, a Compound A (10 mg/kg) administration group, a fentanyl (0.05 mg/kg) administration group, or a fluvoxamine (10 mg/kg) administration group. In the figure, the symbol "*" means $p<0.05$ (vs. vehicle administration group).

Compound A showed a very strong therapeutic effect on pain derived from an emotional component at both concentrations of 5 mg/kg and 10 mg/kg. Also, Compound A showed a significantly excellent therapeutic effect as compared to each existing drug (FIG. 3). Further, experiments using a similar method were carried out for Compounds B, C, F, and G to confirm that they showed therapeutic effects on pain derived from an emotional component.

Experiment 4: Effect of Compound a on Amount of Activity (Experimental Method)

In order to study the effect of Compound A on the amount of activity, Compound A (5 mg/kg or 10 mg/kg) or vehicle (i.e., saline comprising 5% DMSO) was intraperitoneally administered to each mouse, and after 30 minutes, the amount of activity of the mouse was measured for 5 minutes using supermex (Muromachi Kikai Co., Ltd.). In the experiment, the vehicle administration group consisted of 7 mice, the Compound A (5 mg/kg) administration group consisted of 7 mice, and the Compound A (10 mg/kg) administration group consisted of 6 mice.

(Results)

Figure 4:
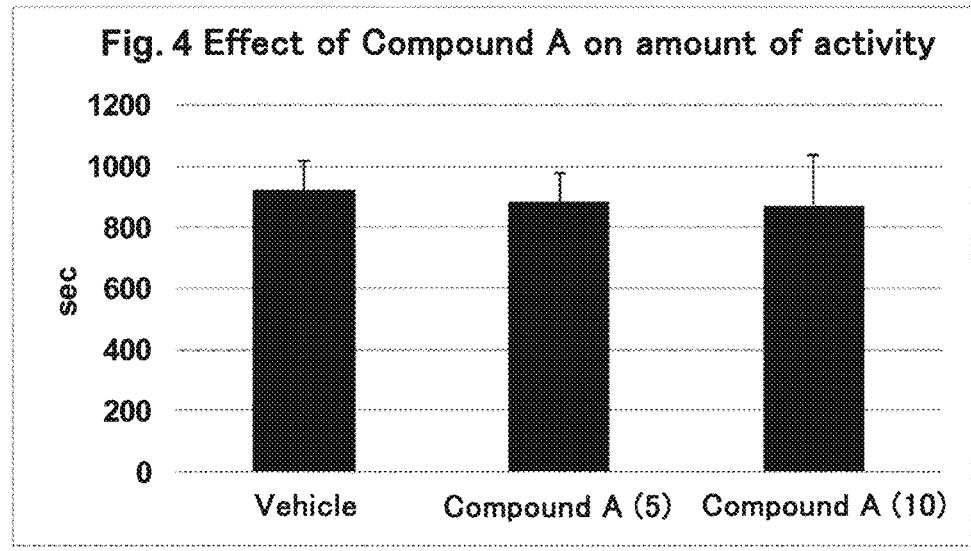
FIG. 4 This figure shows effect of Compound A on the amount of activity. Each bar shows a vehicle administration group, a Compound A (5 mg/kg) administration group, and a Compound A (10 mg/kg) administration group.

Compound A showed no effect on the amount of activity in the intraperitoneal administration at 5 mg/kg and 10 mg/kg (FIG. 4). Namely, it was proved that Compound A did not suppress the amount of activity itself of the mouse. Accordingly, it was proved that the inhibitory effect of Compound A on foot licking and biting caused by the therapeutic effects of Compound A on pain.

Experiment 5: Therapeutic Effects of Compound a on Acute Pain (Experimental Method)

30 minutes before formalin (0.67%, 20 μL) administration, vehicle (i.e., saline comprising 5% DMSO), Compound A (1 mg/kg), Compound A (5 mg/kg), or Compound A (10 mg/kg) was intraperitoneally injected into each mouse. Subsequently, each mouse was placed into the black round box, formalin was administered to the sole of the foot, and then foot licking of the administered foot and biting were measured. Foot licking and biting at 0 to 5 minute(s) were defined as phase 1, and foot licking and biting at 5 to 30 minutes were defined as phase 2. At phase 2, the average time of foot licking and biting for every 5 minutes was calculated. In phase 1, the vehicle administration group consisted of 8 mice, the Compound A (1 mg/kg) administration group (Compound A (1)) consisted of 6 mice, the Compound A (5 mg/kg) administration group (Compound A (5)) consisted of 8 mice, and the Compound A (10 mg/kg) administration group (Compound A (10)) consisted of 8 mice, and in phase 2, the vehicle administration group consisted of 7 mice, the Compound A (1 mg/kg) administration group (Compound A (1)) consisted of 8 mice, the Compound A (5 mg/kg) administration group (Compound A (5)) consisted of 8 mice, and the Compound A (10 mg/kg) administration group (Compound A (10)) consisted of 7 mice.

(Results)

Figure 5:
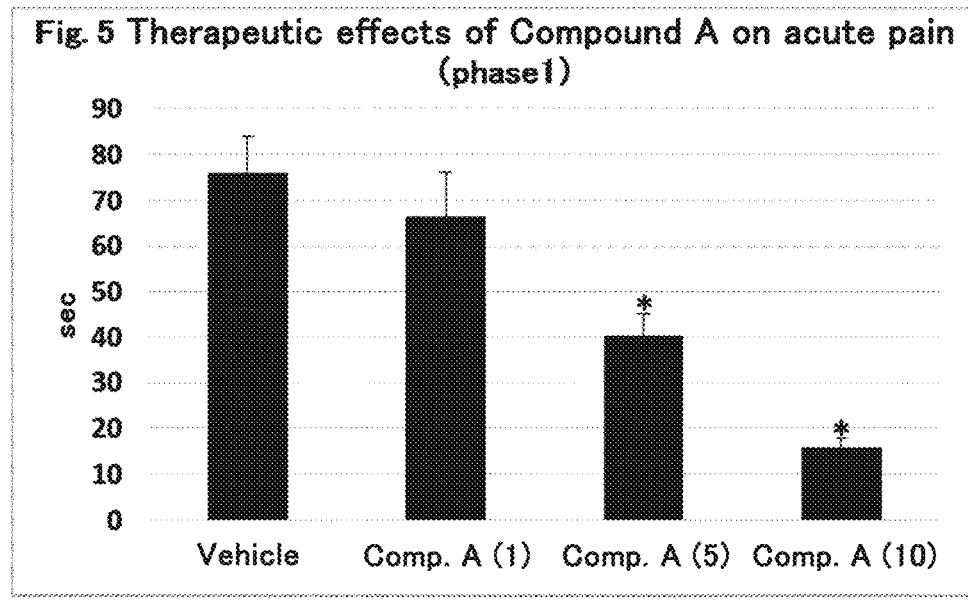
FIG. 5 This figure shows therapeutic effects of Compound A on acute pain in phase 1 (0 to 5 minute(s) after formalin administration). Each bar shows a vehicle administration group, a Compound A (1 mg/kg) administration group, a Compound A (5 mg/kg) administration group, or a Compound A (10 mg/kg) administration group. In the figure, the symbol "*" means $p<0.05$ (vs. vehicle administration group).
Figure 6:
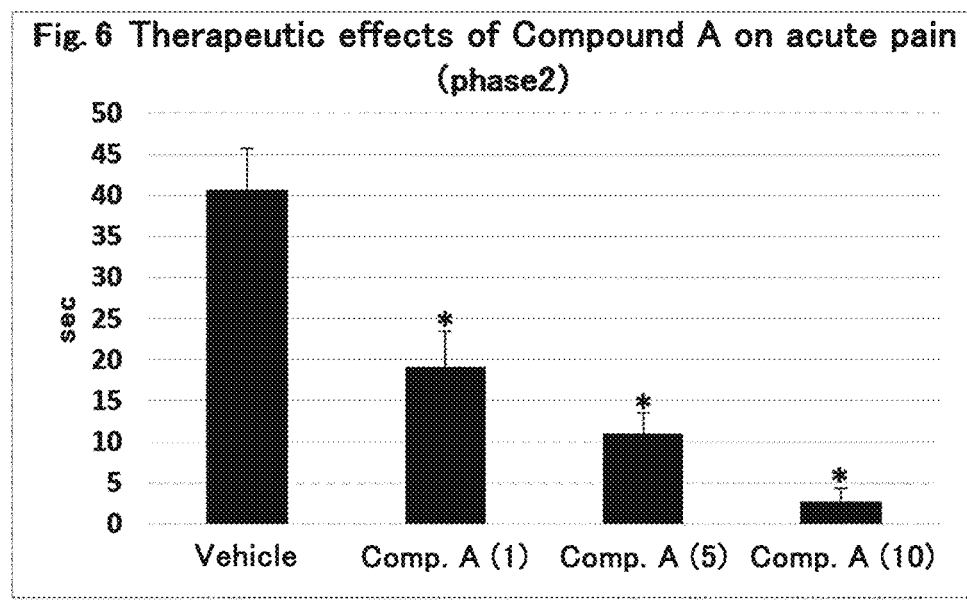
FIG. 6 This figure shows therapeutic effects of Compound A on acute pain in phase 2 (5 to 30 minutes after formalin administration). In the figure, the symbol "*" means $p<0.05$ (vs. vehicle administration group).

Compound A could dose-dependently and significantly suppress foot licking and biting caused by formalin (FIG. 5 and FIG. 6). Namely, Compound A showed excellent therapeutic effects also on acute pain.

INDUSTRIAL APPLICABILITY

The serotonin-3 receptor agonist used as an active ingredient of the present invention has preventive or therapeutic effects on chronic pain on which a sufficient effect has not been achieved by conventional therapeutic agents for pain. Further, the serotonin-3 receptor agonist used as an active ingredient of the present invention has excellent preventive or therapeutic effects also on pain which is believed to be derived from an emotional component. Thus, the present invention can provide an excellent drug for preventing or treating chronic pain and a method for preventing or treating chronic pain. The present invention can also provide an excellent drug for preventing or treating chronic pain and acute pain and a method for preventing or treating chronic pain and acute pain. Further, the present invention can provide a method for screening a compound for preventing or treating chronic pain, the method comprising measuring a serotonin-3 receptor agonist activity.

The invention claimed is:

1. A method for treating chronic pain, the method comprising subcutaneously, intravenously, intraperitoneally, intramuscularly, intrarectally, or orally administering to a patient an effective amount of a serotonin-3 receptor agonist and a pharmaceutically acceptable carrier,
wherein the serotonin-3 receptor agonist is a compound represented by the following formula (I):

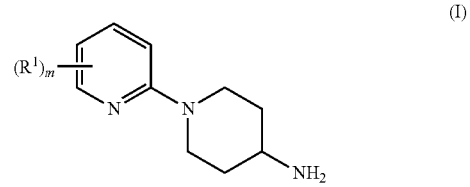

wherein:
m is an integer of 1 to 4; and
$R^1$ is each independently selected from the group consisting of a hydrogen atom, a halogen atom, a methyl group optionally substituted with 1 to 3 halogen atom(s), a methoxy group optionally substituted with 1 to 3 halogen atom(s), and a methylthio group optionally substituted with 1 to 3 halogen atom(s),
or a pharmaceutically acceptable salt thereof.

2. The method according to claim 1, wherein the chronic pain is central dysfunctional pain.

3. The method according to claim 1, wherein the chronic pain comprises pain derived from an emotional component.

4. The method according to claim 1, wherein $R^1$ is each independently a halogen atom.

5. The method according to claim 1, wherein each $R^1$ is a chlorine atom.

6. The method according to claim 1, wherein m is 1.

7. The method according to claim 1, wherein the compound represented by formula (I) or a pharmaceutically acceptable salt thereof is a compound represented by the following formula (I'):

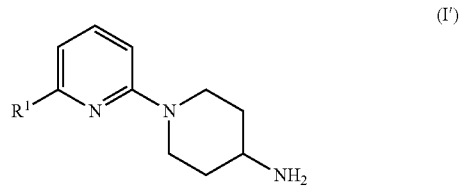

wherein $R^1$ is the same as defined above
or a pharmaceutically acceptable salt thereof.

8. The method according to claim 1, wherein the serotonin-3 receptor agonist is a compound represented by the following formula:

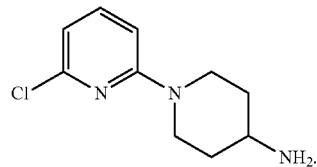 [SMILES: NC1CCN(c2cccc(Cl)n2)CC1]

9. The method according to claim 1 for treating acute pain in addition to chronic pain.

* * * * *